United States Patent
Starr et al.

Patent Number: 5,438,981
Date of Patent: Aug. 8, 1995

[54] AUTOMATIC SAFETY VALVE AND DIFFUSER FOR NASAL AND/OR ORAL GAS DELIVERY MASK

[75] Inventors: John R. Starr, Leechburg; Eric W. Starr, Pittsburgh; William Kaigler, N. Huntingdon; John R. Pujol, Pittsburgh; Pat Devinney, Pittsburgh; Andrew Serowski, Pittsburgh, all of Pa.

[73] Assignee: Respironics, Inc., Murrysville, Pa.

[21] Appl. No.: 129,950

[22] Filed: Sep. 30, 1993

[51] Int. Cl.⁶ .................. A62B 9/02; A62B 18/22; A62B 18/10
[52] U.S. Cl. .................. 128/205.24; 128/207.12; 128/205.25
[58] Field of Search .............. 128/201.24, 201.27, 128/205.24, 205.25, 206.15, 207.12, 204.18, 204.19, 204.23, 204.26

[56] References Cited

U.S. PATENT DOCUMENTS

| | | | |
|---|---|---|---|
| 1,926,027 | 9/1933 | Biggs | 128/205.25 |
| 2,371,965 | 3/1945 | Lehmberg | 128/205.25 |
| 2,438,058 | 3/1948 | Kincheloe | 128/205.25 |
| 3,189,027 | 6/1965 | Bartlett, Jr. | 128/205.24 |
| 3,238,943 | 3/1966 | Holley | 128/205.24 |
| 3,362,420 | 1/1968 | Blackburn et al. | 128/205.24 |
| 3,700,000 | 10/1972 | Hesse et al. | 128/204.19 |
| 3,796,216 | 3/1974 | Schwarz . | |
| 4,304,229 | 12/1981 | Curtin | 128/201.11 |
| 4,606,339 | 8/1986 | Walther | 128/204.19 |
| 4,821,713 | 4/1989 | Bauman | 128/205.13 |
| 4,841,953 | 6/1989 | Dodrill | 128/204.26 |
| 5,042,473 | 8/1991 | Lewis | 128/205.24 |
| 5,065,756 | 11/1991 | Rapoport | 128/205.25 |
| 5,067,487 | 11/1991 | Bauman | 128/205.13 |
| 5,133,347 | 7/1992 | Huennebeck | 128/205.24 |
| 5,140,982 | 8/1992 | Bauman | 128/205.13 |
| 5,273,031 | 12/1993 | Olsson et al. | 128/204.18 |

*Primary Examiner*—Kimberly L. Asher
*Attorney, Agent, or Firm*—Reed Smith Shaw & McClay

[57] ABSTRACT

A self-regulating valve device adapted for use with respiratory equipment of a type which produces a pressurized flow of breathing gas. The valve device affords automatic access to the ambient atmosphere in the event of respiratory equipment malfunction and includes a primary inlet, a secondary inlet and an outlet. The primary inlet is adapted for connection to a ported exhalation valve which, in turn, is connected to one end of an elongated flexible tube, the opposite end of which is connected to a gas flow generator. The outlet, in turn, is connected to the inlet of an oral, nasal or oral/nasal respiratory mask respectively adapted to cover the patient's mouth, nose or mouth and nose. The valve device further comprises a pressure-responsive valve element for regulating gas flow into the inlet of the respiratory mask. In accordance with a further aspect of the invention, there is additionally provided a diffuser element positioned generally at the valve outlet/mask inlet junction. The diffuser element diffuses or disperses the flow of incoming gas (pressurized or ambient) to the mask, whereby the patient's comfort is enhanced while undergoing treatment for sleep apnea, or other respiratory treatment.

14 Claims, 6 Drawing Sheets

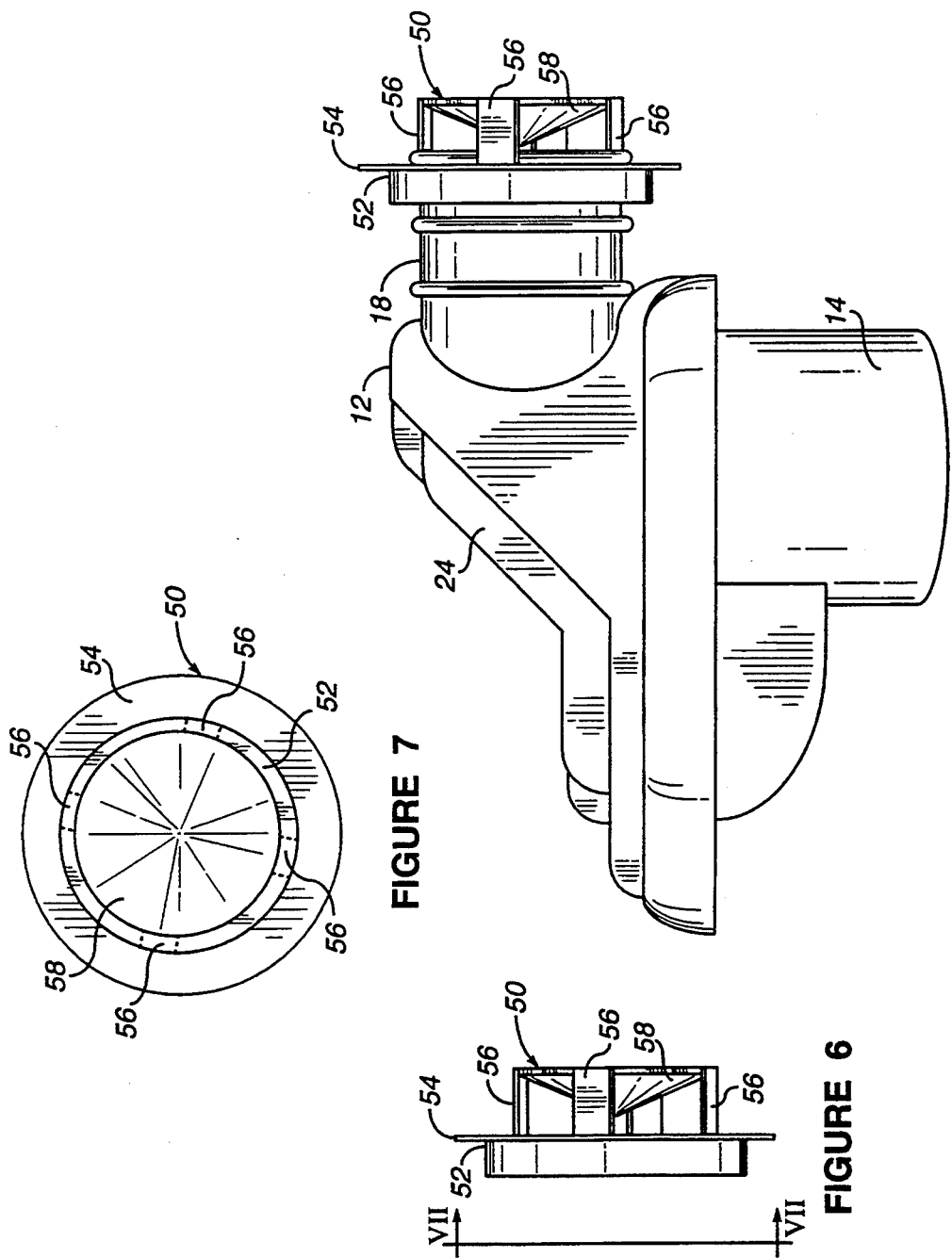

AUTOMATIC SAFETY VALVE AND DIFFUSER FOR NASAL AND/OR ORAL GAS DELIVERY MASK

FIELD OF THE INVENTION

The present invention relates in general to apparatus adapted for use with respiratory equipment and, more particularly, to an automatic safety valve and diffuser adapted for use with a nasal and/or oral gas delivery mask.

BACKGROUND OF THE INVENTION

Valve devices are commonly employed components and perform a variety of functions in myriad respirator apparatus and related breathing assistance equipment. Some, for example, merely turn on and off the gas flow from a supply of pressurized breathing gas. Others include multiposition valves which may provide an individual with access to more than one gas supply or access So a single gas supply by more than one person. Examples of valves used in respiratory apparatus may be found in U.S. Pat. Nos. 3,238,943, 4,304,229, 4,841,953 and 5,133,347.

More specifically, U.S. Pat. No. 3,238,943 discloses a breathing system which includes a first face mask and a breathing selector in which the selector has two valve seats to permit passage of air to either the first face mask or to the first face mask and a second face mask, in order to permit breathable air to be accessed by more than one party from the same air supply.

U.S. Pat. No. 4,304,229 discloses an underwater breathing device including a two-way selection valve which permits a diver to selectively employ either an air supply tank or a snorkel for outside air.

U.S. Pat. No. 4,841,953 discloses an auxiliary air supply system for a breathing apparatus in which an auxiliary source of air is selectively accessed by the user and provided to a face piece independent of the normal air supply. The auxiliary air may be provided to the user if the standard breathing apparatus malfunctions.

U.S. Pat. No. 5,133,347 teaches a mouthpiece valve for respiratory equipment which includes a valve disk operable to close the respiratory gas flow connection to the equipment when the equipment is not in use. The mouthpiece valve may be subsequently unlocked by a single hand motion of the user when the breathing equipment is to be used.

While the valve devices suggested by these systems are effective for their intended purposes, they would be of limited practical use in situations where the user of the breathing equipment were unconscious, e.g., a sleeping patient undergoing assisted ventilation treatment for sleep apnea syndrome. Indeed, for the aforementioned valve devices to be properly operated, they require the selective acts of a conscious individual. Manifestly, a sleeping or otherwise unconscious person is incapable of such acts.

When experiencing assisted ventilation treatment, a sleep apnea sufferer typically breathes through an oral, nasal or oral/nasal respiratory mask which respectively covers the wearer's mouth, nose or mouth and nose. The mask inlet opening is connected to one end of an elongated flexible tube, the opposite end of which is connected to a gas flow generator means (e.g., a blower, or the like) for providing a flow of pressurized air. However, none of the presently known breathing assistance systems used for sleep apnea treatment are believed to be equipped with air source bypass systems. Thus, should the air source malfunction or the pressurized air supply be otherwise cut off, the unconscious patient may not have ready access to the ambient atmosphere.

In this regard, much of the time spent wearing a breathing mask during sleep apnea treatment is while the user is asleep. Consequently, even if manually operated valves providing access to the ambient atmosphere in the event of air source failure were available, they would be of no practical use to an unconscious patient. The sole avenue of relief for the patient is to awaken, remove the mask and breathe through his mouth and/or nose.

Non-rebreathing valves (NRVs) constitute another class of known valves designed for particular use with respiratory equipment. Such valves are usually connected proximate to a breathing mask inlet opening and include a respiratory gas inlet, a respiratory gas outlet and a user's expiratory gas exhaust passageway open to the atmosphere. The purpose of such valves is to permit the flow of pressurized respiratory gas to the user upon user inhalation and to prevent the flow of respiratory gas and permit exhaust of the user's expiratory gases upon exhalation. A typical NRV construction includes an inlet surrounded in the interior of the valve housing by a bellows-like, resilient diaphragm which supports an annular valve seat member which is biased by the diaphragm to seat against an internal shoulder of the valve housing. The valve seat member is provided with a central aperture over which is positioned a flapper valve element biased to cover the aperture. The bias of the valve element is minimal. Consequently, the valve element may become displaced from the aperture under the mild flow of pressurized respiratory gas and/or a user's inhalation force whereby the respiratory gas may pass to the user's airway. Upon exhalation, the force of the expiratory gases closes the flapper valve element thereby sealing the aperture while simultaneously displacing the annular valve seat from the housing shoulder against the bias of the diaphragm such that the expiratory gases may escape through the exhaust passageway. This operation is repeated for each of the user's respiratory cycles and functions quite well so long as the pressurized gas source is operational and supplying a flow of respiratory gas.

However, should the supply of respiratory gas be cut off (e.g., the gas conduit becomes kinked), the user would evacuate any breathing gas remaining upstream of the NRV within a few inhalations. Upon total evacuation, gas flow through the aperture would cease and the diaphragm would bias the annular valve seat against the internal valve housing shoulder. At this point in time, the NRV would for practical purposes cease to function. That is, it would be operable only to exhaust the user's expiratory gases. In other words, although the user's exhalation immediately following total evacuation of the breathing gas supply upstream of the NRV would raise the annular valve seat from the housing shoulder against the bias of the diaphragm and thereby enable the expiratory gas to be discharged through the exhaust passageway, that exhalation would necessarily be followed by an inhalation whose force (in combination with the diaphragm bias) would cause the annular valve seat to engage the valve housing shoulder, whereby the user would be cut off from breathing gas of any kind, i.e., either from the pressurized gas source or the ambient atmosphere. At this point, the user would have to remove the mask in order to breathe. In the case of a sleeping user, such as a patient undergoing sleep apnea treatment, the patient would therefore be awakened upon failure of the respiratory gas supply, thereby defeating the central purpose of the treatment, namely, uninterrupted, therapeutic and restful sleep.

The reader will readily appreciate that the detrimental impact upon the patient's sleep patterns (which are intrinsically hindered by the episodic upper airway obstructions associated with sleep apnea) is thus compounded by the additional disturbances attendant to air source malfunctions. More particularly, those afflicted with sleep apnea experience sleep fragmentation and intermittent, complete or nearly complete cessation of ventilation during sleep with potentially severe degrees of oxyhemoglobin unsaturation. These symptoms may be translated clinically into debilitating daytime sleepiness, cardiac dysrhythmias, pulmonary-artery hypertension, congestive heart failure and cognitive dysfunction. Other consequences of sleep apnea include right ventricular dysfunction with cot pulmonale, carbon dioxide retention during wakefulness as well as during sleep, and continuous reduced arterial oxygen tension. In extreme cases, hypersomnolent sleep apnea patients may be at an elevated mortality risk from these factors as well as from accidents while driving and/or operating potentially dangerous equipment. Hence, by eliminating air source obstruction/malfunction problems, sleep apnea treatment may proceed with efficacy, thereby minimizing the damaging effects experienced by sleep apnea sufferers.

Another drawback to known sleep apnea treatment systems is that some patients find the direct facial impingement of the incoming breathing gas flow (as well as other effects of the treatment) to be-so uncomfortable and/or distracting that they cannot tolerate the therapy. As a result, compliance with the treatment by comparatively sensitive patients is somewhat less than the general patient population, whereby those patients are effectively precluded from the therapeutic benefits of the treatment.

An advantage exists, therefore, for a safety valve device adapted for use with respiratory equipment of a type which provides a pressurized flow of breathing gas, which valve device would be self-regulating and pressure-responsive so as to provide access to the ambient atmosphere in the event of malfunction of the respiratory equipment.

A further advantage exists for a diffuser element adapted for positioning in the inlet of the breathing mask which enhances the user's comfort during sleep apnea treatment by diffusing or dispersing the flow of breathing gas as it enters the respiratory mask.

SUMMARY OF THE INVENTION

According to the present invention, there is provided a valve device adapted for use with respiratory equipment of a type which produces a pressurized flow of breathing gas. The valve device affords automatic access to the ambient atmosphere in the event of respiratory equipment malfunction and includes a primary inlet, a secondary inlet and an outlet. Pursuant to the presently preferred embodiment, the primary inlet is adapted for connection to a conventional ported exhalation valve which, in turn, is connected to one end of an elongated flexible tube, the opposite end of which is connected to a gas flow generator means or air source (e.g., a blower or the like). The outlet, in turn, is connected to the inlet of an oral, nasal or oral/nasal respiratory mask respectively adapted to cover the patient's mouth, nose or mouth and nose. It is also contemplated that the valve device may be suitably constructed such that it may be positioned at any point between the gas flow generator means and the respiratory mask. The valve device further comprises a valve element for regulating air flow into the inlet of the breathing mask. Although normally biased so as to block the primary inlet, the valve element is caused to open the primary inlet and close the secondary inlet under the influence of even a gentle flow of pressurized air from the air source. Should that air flow cease, e.g., the air source either malfunctions or the flexible hose becomes kinked, the bias of the valve element causes the element to close the primary inlet and open the secondary inlet, which inlet communicates with the ambient atmosphere. As a consequence, and without disturbing the patient, the valve element automatically provides access to atmospheric air in the event of any failure of the pressurized air source.

In accordance with a further aspect of the invention, there is additionally provided a diffuser element positioned generally at the valve outlet/mask inlet junction. The diffuser element diffuses or disperses the flow of incoming gas (pressurized or ambient) to the mask, whereby the patient's comfort is enhanced while undergoing treatment for sleep apnea, or other assisted respiratory treatment.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings wherein:

FIG. 6 is a side elevation view of a preferred embodiment of the gas diffuser element of the present invention;

FIG. 7 is a view of the gas diffuser element from line VII—VII of FIG. 6;

FIG. 8 is a view of the gas diffuser element mounted to the valve device of FIG. 1.

DETAILED DESCRIPTION OF THE INVENTION

Figure 1:
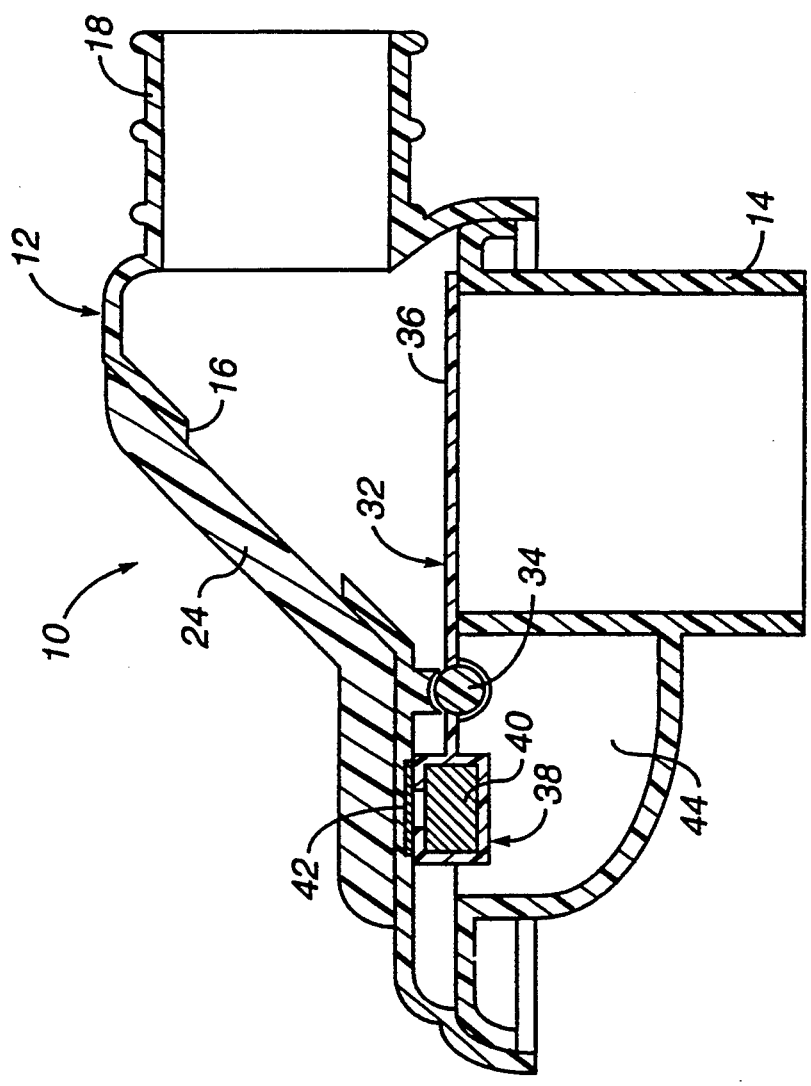
FIG. 1 is vertical cross-section of a first embodiment of the valve device of the present invention with the valve element thereof depicted in a first position covering the primary inlet of the valve device.
Figure 2:
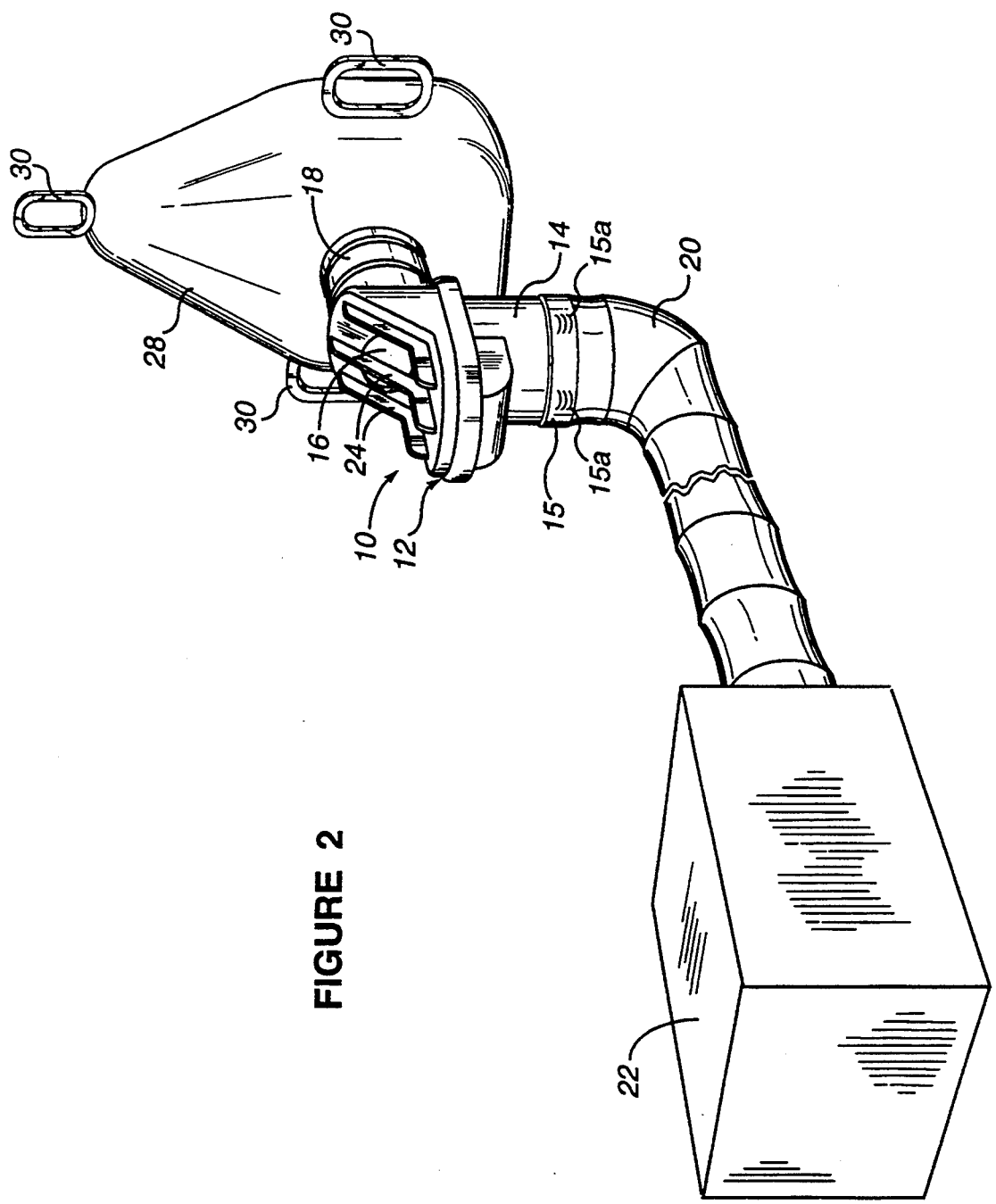
FIG. 2 is a perspective view of the valve device of the present invention in a respirator system including a gas flow generator, a gas delivery tube and a respiratory mask.

There is generally indicated at 10 in FIGS. 1 and 2 a valve device 10 according to a first presently preferred embodiment of the instant invention. Valve device 10 preferably comprises a housing 12 including a primary inlet 14, a secondary inlet 16 and an outlet 18. The housing is preferably formed of durable material such as high-strength plastic or metal. As shown in FIG. 2, the primary inlet 14 is normally connected to a conventional exhalation valve 15 having exhaust ports 15a, which in turn is connected to one end of an elongated flexible conduit or gas delivery tube 20, the opposite end of which is connected to a gas flow generator means or air source 22 (e.g., a blower or the like). The secondary inlet 16 is open to the ambient atmosphere and is protected from unintended blockage by means such as raised vanes 24, a grate, or the like, while the outlet 18 is typically connected to an inlet 26 (FIG. 9) of a respiratory mask 28. As is known, during treatment the mask 28 is typically secured to the wearer's head with straps (not illustrated) threaded through retention tabs 30 such that an effective and substantially gas-tight but comfortable seal is created between the user's face and the mask. Additionally, the valve device may be constructed in a manner whereby it can be incorporated into the respiratory mask 28 or positioned at any point between the gas flow generator means 22 and the respiratory mask. Placements other than the vicinity of the mask inlet, however, are generally not preferred because increasing quantities of exhaled carbon dioxide tend to be retained in the flexible hose the more distant the valve device is situated with respect to the mask. Additionally, it will be appreciated that the mask may be an oral/nasal mask for covering a wearer's mouth and nose (similar to the mask disclosed in U.S. Pat. No. 4,907,584), an oral (mouth-covering) or a nasal (nose-covering) respiratory mask.

Further according to the present invention, the valve device housing 12 includes a self-regulating valve element 32 that controls gas flow through the primary and secondary inlets 14 and 16, whereby the valve element regulates gas flow into the inlet 26 of the breathing mask. The valve element 32 is constructed and arranged such that it is responsive to either positive pressure produced by the gas flow generator means or negative pressure produced by a user's inhalation.

Pursuant to a presently preferred embodiment, the valve element is formed as a generally planar and substantially rigid member pivotally supported at an intermediate region thereof by outwardly and oppositely directed, colinear pivot pins 34 which are journaled within bearing formations provided in housing 12. The valve element further includes a closure portion 36 of dimensions sufficient to cover the primary and secondary inlets 14 and 16 when positioned respectively thereover.

Figure 3:
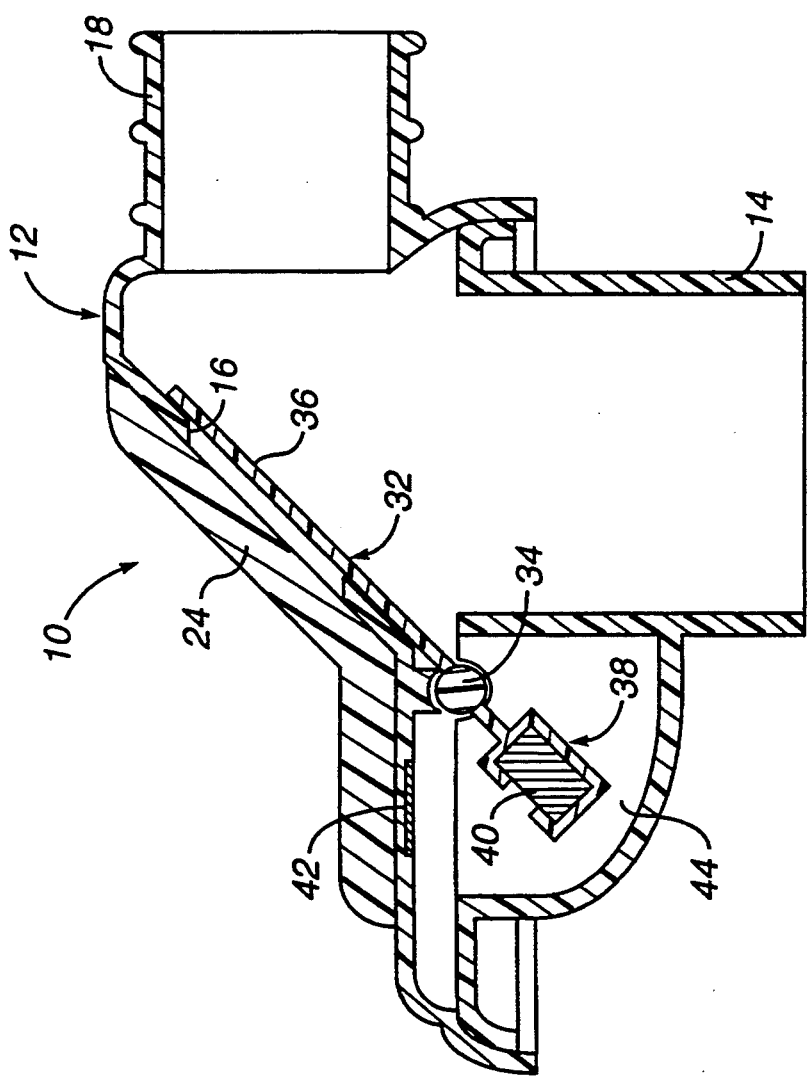
FIG. 3 is a view similar to FIG. 1 with the valve element of the valve device being depicted in a second position covering the secondary inlet of the valve device.

As shown most clearly in FIGS. 1 and 3, the valve element 32 is desirably constructed such that it is as nearly weight-balanced as possible with respect to the pivot axis formed by pivot pins 34. Preferably, therefore, closure portion 36 is counterpoised by counterweight means 38 of substantially the same weight as that of the closure portion. As a consequence, due to the coefficient of friction between the pivot pins 34 and their associated valve housing bearing formations, as well as the intrinsic inertia of the valve element 32, once the valve element is disposed such that the closure portion 36 thereof covers either the primary inlet 14 (FIG. 1) or the secondary inlet 16 (FIG. 3), the valve element tends to remain in that position until acted upon by a displacement force. In a first operative embodiment, that displacement force is provided by (depending upon the position of valve element 32) either positive pressure associated with the flow of pressurized respiratory gas from the gas flow generator means 22 or negative pressure resulting from the user's first inhalation following a cessation of the pressurized respiratory gas flow.

More specifically, when the mask 28 is first donned by the user the valve element 32 is normally oriented such that closure portion 36 covers the primary inlet 14. The user then activates she gas flow generator means 22 to produce a flow of pressurized gas in conduit 20. The positive gas pressure thus applied against the underside of the closure 36, because of the virtual balance of valve element 32 with respect to pivot pins 34, causes the valve element 32 to pivot upwardly until the closure portion covers the secondary inlet 16. Thereafter, the inertia of the valve element 32, the friction between the pivot pins 34 and their associated valve housing bearing formations, and the positive pressure gas flow from the gas flow generator means maintains the valve element in such position. To accommodate the path of movement of the counterweight means 38 as the valve element swings between a first position closing the primary inlet and a second position closing the secondary inlet, the housing is desirably formed with an interior cavity 44.

Should the pressurized respiratory gas flow then be cut off for any reason, the user's next inhalation following such gas flow cessation would exert a negative pressure force on the underside of the closure member 36, thereby causing the valve element 32 to pivot downwardly and cover the primary inlet 14. With the valve element so disposed, the user would have complete access to ambient air through secondary inlet 16. This situation would continue until such time that the pressurized gas flow is restored, whereupon the positive pressure produced by the pressurized gas would again compel the valve element 32 to pivot upwardly whereby closure portion 36 would cover secondary inlet 16 and assisted ventilation would proceed.

To minimize flutter of the valve member 32 as it pivots between its first and second positions, the counterweight means 38 preferably includes suitable motion damping means. A presently preferred form of such means include a small permanent magnet 40 affixed proximate a first end of the valve element, which magnet is magnetically attracted to a small metallic, and magnetically responsive, e.g., steel, strip 42 affixed to the interior of the housing 12. It will be appreciated that the respective positions of the permanent magnet 40 and metallic strip 42 may be reversed, if desired. Alternatively, two magnets 40 may be employed, one affixed to the housing and the other to the valve element. Still further, a small electromagnetic system connected to the gas flow generator means power source would also produce favorable results.

Moreover, the permanent magnet 40 may be selected to be one having a magnetic force of such inconsequential magnitude that it does not exert any practical biassing force upon the valve member when such member is upwardly pivoted to cover the secondary inlet 16 (and only minimal magnetic attraction to strip 42 when the valve member is downwardly pivoted to cover the primary inlet). Similarly, the permanent magnet may be selected so that it demonstrates a material, albeit limited, attraction to strip 42 when the valve member is upwardly pivoted and covering the secondary inlet. In this situation, the magnet 40 and strip 42 act as a means for biassing the valve member into a position whereby closure member 36 covers the primary inlet 14.

Other biassing means may be efficaciously employed to produce the same result, such as, for example, an appropriately positioned leaf, tension, compression or torsion spring. It is vital, however, that the biassing force exerted by the biassing means be capable of yielding to the gentle pressurized gas flows that are typical of sleep apnea and other respiratory treatments.

During normal operation the gas flow from the gas flow generation means 22 which passes through the primary inlet is sufficient to overcome the biassing force of the biassing means. When this occurs, the valve element is caused to pivot about the pins 38 such that the closure portion 36 is raised upwardly from a first seated position covering the primary inlet 14 to a second seated position covering the secondary inlet 16, as is depicted in FIG. 3. With the valve element so oriented due to the pressurized gas flow, the assisted respiratory treatment proceeds unhindered and access to the ambient atmosphere is effectively precluded.

In the event gas flow should cease, e.g., the air source 22 malfunctions or the flexible hose 20 becomes kinked, the biassing means urges the valve element 32 to pivot downwardly, whereby the closure portion 36 covers the primary inlet 14 while exposing the secondary inlet 16. With the valve element so disposed, the user has unrestricted access to the ambient atmosphere until such time that the gas flow from the gas flow generator means is restored, whereupon the primary inlet 14 is again opened and the secondary inlet 16 is closed. Hence, the present invention provides an apparatus wherein the user at all times has unimpeded access to breathing gas, either pressurized or ambient, and regardless of whether the valve element is biased or unbiased. Consequently, the user's comfort and safety are enhanced during periods of both wakefulness and sleep, and the likelihood that the user's sleep would become disturbed by a malfunction of the pressurized breathing gas source is markedly reduced.

Figure 5:
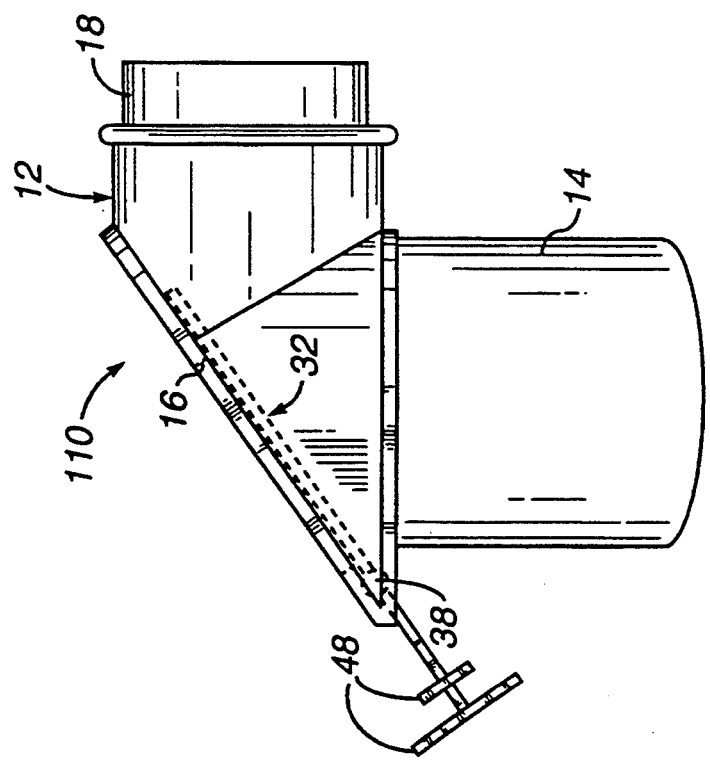
FIG. 5 is an elevational view similar to FIG. 4 with valve element depicted in a second position covering the secondary inlet.
Figure 4:
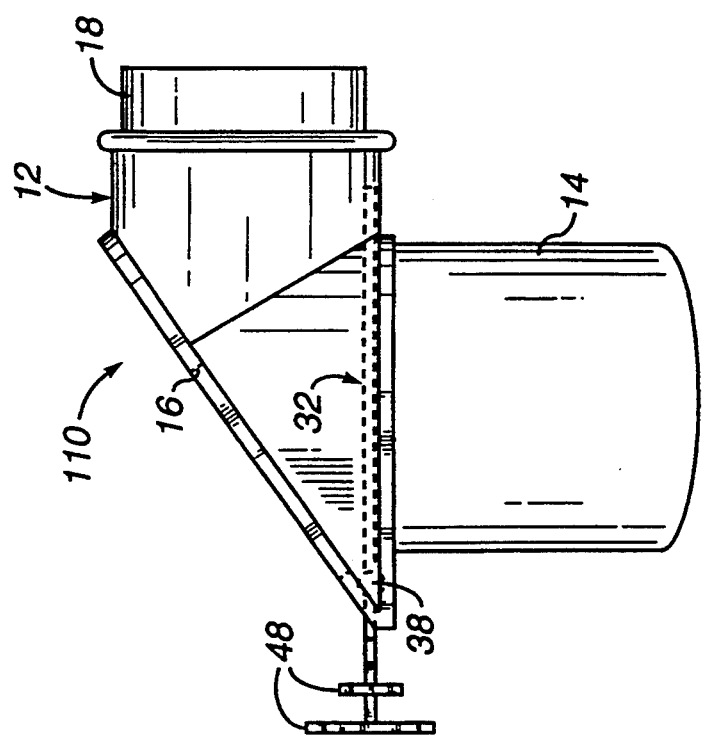
FIG. 4 is an elevational view of a second embodiment of the valve device of the present invention with the valve element thereof depicted in a first position covering the primary inlet.

Referring to FIGS. 4 and 5, where like references represent elements similar to those thus far discussed, there is depicted a further embodiment of the valve device of the present invention designated by reference numeral 110. Valve device 110 operates and is constructed substantially similar to valve device 10; hence, only those aspects of valve device 110 which measurably depart from valve device 10 will be discussed in detail, except where otherwise necessary for purposes of clarity. According to this embodiment, the valve element 32 is balanced for pivotal movement by one or more weight elements 48. As with the earlier described counterweight means 38, the inherent balance of the system of FIGS. 4 and 5 is such that it is overcome by a gentle flow of pressurized gas from the gas flow generator means. Again, when that balance is overcome by the gas flow, the primary inlet 14 and the valve outlet 18 are in fluid communication. Conversely, when the pressurized gas supply is cut off, the user's inhalation affords the user access to the ambient atmosphere by exposing secondary inlet 16.

Variations of the above-described valve devices are contemplated by the inventor and are considered to be within the scope of the present invention. For example, in lieu of a pivotally supported valve element, that element may instead be flap anchored to the housing 12. The flap may be formed of material suitable to assume a bias whereby the flap covers the primary inlet 14 in the absence of gas flow but also flexible enough to be deflected by the gas flow to effectively seal the secondary inlet 16. Alternatively, the valve element may be a lightweight (e.g., cork, polystyrene, or the like) and lightly-biased ball element. Such ball element would be constrained to travel within a cage between the primary inlet and the secondary inlet and dimensioned to sealingly cover the appropriate inlet in response to the presence or absence of gas flow from the gas flow generator means. A further alternative would be a valve of the cuff piston type. The foregoing should not be construed to be limitative but merely illustrative of the types of valve mechanisms which would find beneficial use in connection with the valve device of the present invention. The only material functional limitations of such mechanism is that it be self-regulating in the sense that it operates to open the primary inlet and close the secondary inlet under the force of a flow of pressurized respiratory gas, and to close the primary inlet and open the secondary inlet upon the user's initial inhalation following cessation of the flow of pressurized respiratory gas.

Although described in connection with its presently preferred application, i.e., for use in communicating respiratory gases, it will be appreciated that the valve device 10 is not intended to be, nor should it be construed to be, exclusively limited thereto. That is, the valve device of the present invention may also be incorporated into suitable apparatus so as to communicate other fluids such as liquids or non-respiratory gases.

FIGS. 6 through 8 illustrate a further feature of the present invention, specifically a diffuser element designated by reference numeral 50 which is adapted for beneficial use with either embodiment of the valve device of the present invention described above, any variants thereof encompassed with the scope of the attached claims or any assisted respiratory equipment of the type including a source of pressurized gas, a flexible gas conduit and a respiratory mask. Diffuser element 50 includes means for diffusing or dispersing breathing gas (pressurized or ambient) as it enters the respiratory mask 28, whereby the patient's comfort is enhanced while undergoing treatment for sleep apnea or other pressurized gas respiratory treatment.

Figure 9:
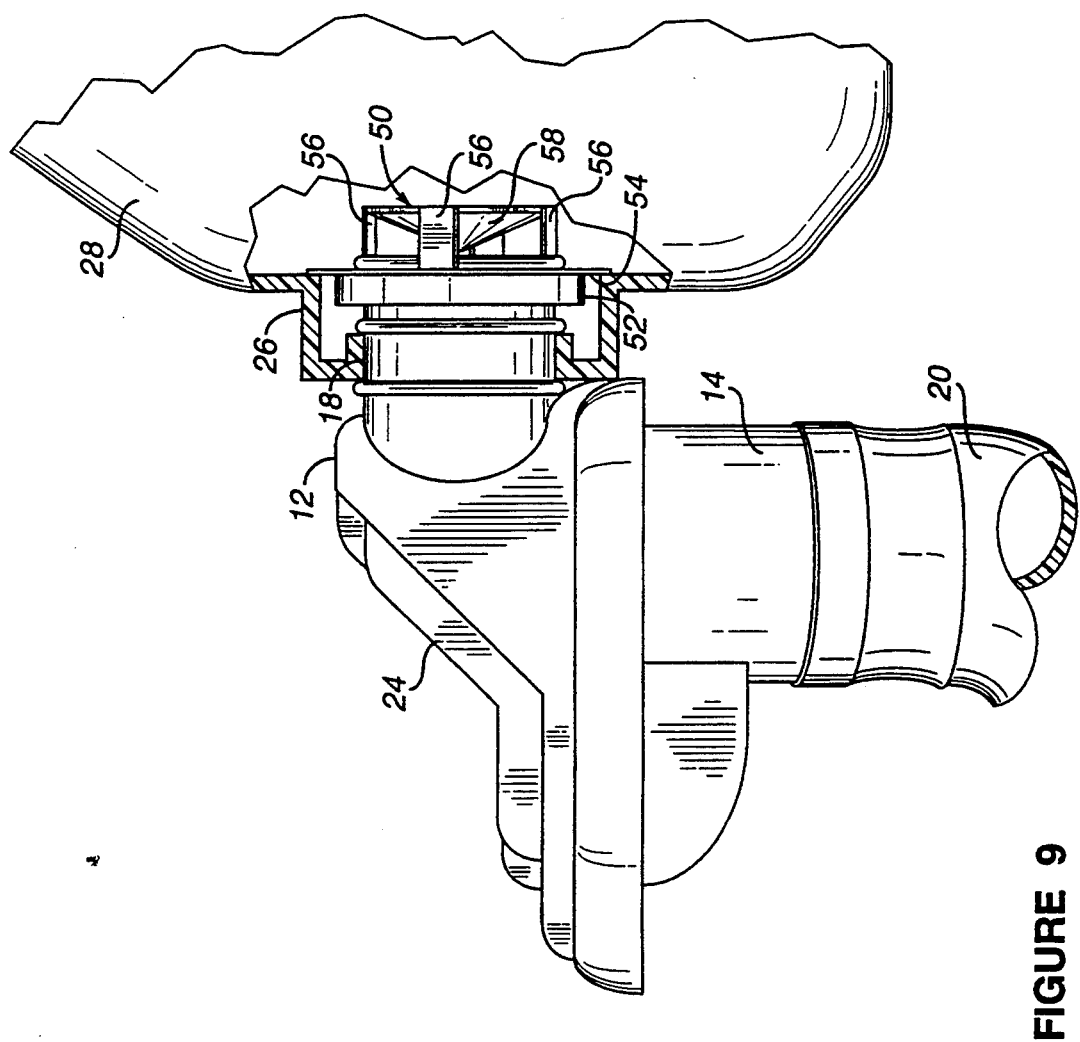
FIG. 9 is a cut-away elevation view, in partial section, of the valve device and gas diffuser element of the present invention connected to a gas flow tube and a respiratory mask.

The diffuser element 50 preferably includes an annular engagement ring 52 sized to tightly yet releasably receive the outlet 18 of the valve device 10 or 110 and a flexible, radially projecting annular flange 54 which is adapted to yieldably engage and seal the interior of the respiratory mask immediately surrounding the mask inlet 26 from the ambient atmosphere in the manner shown in FIG. 9. Desirably, the diffuser element is manufactured as a unitary molded structure formed of rubber, neoprene, resilient plastic, or the like, whereby the engagement ring 52 yieldably and sealing receives the outlet 18 of the valve device. Extending from the side of the annular flange 54 opposite the engagement ring is a plurality of spaced supports 56 to which is joined a diffusing means 58. According to the presently preferred construction, the diffusing means is a tapered, preferably conical, member whose apex, when the diffuser element is properly installed, is directed opposite to the direction of gas flow into the mask. As such, the direction of the incoming gas flow is changed by the diffusing means 58 in such fashion that the gas discharged by the valve device outlet 18 is directed by the diffusing means to be discharged between the spaced supports 56 and away from direct impingement upon the mask wearer's face.

While shown in its preferred application, i.e., in combination with the valve device 10 or 110, it will be appreciated that the diffuser element 50 of the present invention may also be advantageously employed with respiratory equipment in the absence the instant valve device. That is to say, the diffuser element can be joined to a suitable mask 28 and appropriately sized so as to directly and sealingly receive the end of a flexible gas delivery tube such as the tube 20 shown in FIG. 2.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is

1. Apparatus adapted for use with respiratory equipment, said apparatus comprising, in combination:
   a self-regulating valve device comprising:
   a housing including a primary inlet adapted for connection to a source of pressurized gas, a secondary inlet in communication with an ambient atmosphere, and an outlet; and
   a substantially rigid valve element and means for pivotally mounting said valve element within said housing, said valve element being operable to open said primary inlet and close said secondary inlet in the presence of a flow of pressurized gas from said pressurized gas source and to open said secondary inlet and close said primary inlet in the absence of said flow of pressurized gas, said valve element comprising a closure portion dimensioned to cover said primary and secondary inlets and means for counterbalancing said closure portion with respect to said pivotally mounting means; and
   a gas diffuser element comprising:
   means for receiving said outlet;
   means for sealing a region surrounding an inlet of a respiratory mask from an ambient atmosphere; and
   means for diffusing a flow of gas discharged by said outlet.

2. The apparatus of claim 1 further comprising means for biassing said valve element into a position closing said primary inlet.

3. The apparatus of claim 1 wherein said diffusing means comprise means for changing direction of said flow of gas discharged by said outlet.

4. The apparatus of claim 1 wherein said means for changing direction of said flow of gas discharged by said outlet includes a tapered member having an apex directed substantially opposite to a flow direction of said flow of gas discharged by said outlet.

5. The apparatus of claim 1 wherein said diffuser element is formed as a unitary structure.

6. The apparatus of claim 5 wherein said diffuser element is formed of resilient material.

7. Apparatus for delivering pressurized gas to the airway of a patient, said apparatus comprising:
   gas flow generator means for providing a flow of said pressurized gas;
   conduit means for delivering said gas flow to the airway of said patient;
   a respiratory mask having an inlet; and
   a self-regulating valve device comprising:
   a housing including a primary inlet adapted for connection to said conduit means, a secondary inlet in communication with an ambient atmosphere, and an outlet adapted for connection to said respiratory mask inlet; and
   a substantially rigid valve element and means for pivotally mounting said valve element within said housing, said valve element being operable to open said primary inlet and close said secondary inlet in the presence of a flow of pressurized gas from said pressurized gas source and to open said secondary inlet and close said primary inlet in the absence of said flow of pressurized gas, said valve element comprising a closure portion dimensioned to cover said primary and secondary inlets and means for counterbalancing said closure portion with respect to said pivotally mounting means.

8. The apparatus of claim 7 further comprising means for biassing said valve element into a position closing said primary inlet.

9. Apparatus for delivering pressurized gas to the airway of a patient, said apparatus comprising:
   gas flow generator means for providing a flow of said pressurized gas;
   conduit means for delivering said gas flow to the airway of said patient;
   a respiratory mask having an inlet;
   a self-regulating valve device comprising:
   a housing including a primary inlet adapted for connection to said conduit means, a secondary inlet in communication with an ambient atmosphere, and an outlet; and
   a substantially rigid valve element and means for pivotally mounting said valve element within said housing, said valve element being operable to open said primary inlet and close said secondary inlet in the presence of a flow of pressurized gas from said pressurized gas source and to open said secondary inlet and close said primary inlet in the absence of said flow of pressurized gas, said valve element comprising a closure portion dimensioned to cover said primary and secondary inlets and means for counterbalancing said closure portion with respect to said pivotally mounting means; and
   a gas diffuser element comprising:
   means for receiving said outlet;
   means for sealing a region immediately surrounding said respiratory mask inlet from an ambient atmosphere; and
   means for diffusing a flow of gas discharged by said outlet.

10. The apparatus of claim 9 further comprising means for biassing said valve element into a position closing said primary inlet.

11. The apparatus of claim 9 wherein said diffusing means comprise means for changing direction of said flow of gas discharged by said outlet.

12. The apparatus of claim 11 wherein said means for changing direction of said flow of gas includes a tapered member having an apex directed substantially opposite to a flow direction of said flow of gas discharged by said outlet.

13. The apparatus of claim 9 wherein said diffuser element is formed as a unitary structure.

14. The apparatus of claim 13 wherein said diffuser element is formed of resilient material.

* * * * *